United States Patent [19]
Elliott

[11] Patent Number: 4,975,249
[45] Date of Patent: Dec. 4, 1990

[54] OPTICAL AND CAPACITANCE TYPE, PHASE TRANSITION, HUMIDITY-RESPONSIVE DEVICES

[76] Inventor: Stanley B. Elliott, 7125 Conelly Blvd., Walton Hills, Ohio 44146

[21] Appl. No.: 444,559

[22] Filed: Dec. 1, 1989

Related U.S. Application Data

[63] Continuation of Ser. No. 78,186, Jul. 27, 1987.

[51] Int. Cl.$^5$ .............................................. G01N 31/00
[52] U.S. Cl. ....................................... 422/83; 436/39; 73/29.1; 73/335; 73/336.5; 252/963
[58] Field of Search ....................... 422/57, 83; 436/39; 73/29, 73, 335, 336, 336.5; 252/299.61, 962, 963; 350/404, 406

[56] References Cited

U.S. PATENT DOCUMENTS

| | | |
|---|---|---|
| 3,776,038 | 12/1973 | Elliott . |
| 3,927,977 | 12/1975 | Jacobs .................................... 422/83 |
| 4,166,891 | 9/1979 | Elliott . |
| 4,175,207 | 11/1979 | Elliott . |
| 4,276,128 | 6/1981 | Nishino et al. .................... 204/38 A |
| 4,473,813 | 9/1984 | Kinjo et al. ............................ 338/35 |
| 4,500,940 | 2/1985 | Kuisma et al. ...................... 361/286 |
| 4,681,855 | 7/1987 | Huang .................................... 436/39 |

OTHER PUBLICATIONS

Chemical Abstracts 86:163983n, Noda et al., 6-1977.

*Primary Examiner*—Robert J. Warden
*Assistant Examiner*—D. John Griffith, Jr.
*Attorney, Agent, or Firm*—Baldwin, Egan & Fetzer

[57] ABSTRACT

The invention provides novel chemical compositions for use in primary, optical/capacitance hygrometric devices. It also provides methods for using these compositions as sensors for the precise measurements of the humidity of gases as well as the apparatus. The chemical compositions, which of themselves sense the change in water vapor pressure, are birefringent, translucent, and anisotropic at a first water vapor pressure/temperature, but non-birefringent, optically clear, and isotropic at a second vapor pressure/temperature. Optical changes which accompany these phase changes may be amplified. Some compositions, exhibit abrupt and large increases in their dielectric constant coincident with the optical changes which occur at the phase shift point. Others show a large and precisely linear change in dielectric constant over many decades of relative humidity (RH), but the optical shift occurs at a precise point within the range. By noting the capacitance readout from a prestandardized combination optical/capacitance hygrometric device at the moment of optically indicated phase shift (when the system changes from isotropic to birefringent), any drift in the electronics of the device can be immediately detected since the sensor's phase shift point is invariant. If it is desired to eliminate polarizer amplifiers because of their cost, sensor substrates can be shaped so that internal reflection within the substrate and optical coupling of the birefringent sensor to the substrate generate excellent optical signals at the sensor's trigger points. The devices and methods of the new hygrometry allow many variations on the primary requirements. If desire, the sensor can be made an integral part of a capacitance-sensitive IC.

41 Claims, 4 Drawing Sheets

OPTICAL AND CAPACITANCE TYPE, PHASE TRANSITION, HUMIDITY-RESPONSIVE DEVICES

This is a continuation patent application of U.S. Ser. No. 07/078,186 filed Jul. 27, 1987.

BACKGROUND OF THE INVENTION

In my pending patent application, U.S. Ser. No. 763,003, I have noted that scores of hygrometric devices have been developed in response to a world wide need among modern societies for the indication and control of the humidity of myriad processes and locations in commerce, industry, and the sciences. I particularly stressed that nearly all of these devices have been "secondary" types which depend on non-reproducible processes such as moisture sorption by various materials. As a result, the devices have no inherent accuracy, they drift badly over a period of time, and they are not suitable for myriad demanding needs.

In my pending application I noted that only a few inherently accurate "primary" type devices based on unvarying physical phenomena have been developed. These have been characterized by high cost, high power consumption, and large sensor bulk and equipment size. Heading the short list of primary devices has been the "dew temperature" or "cold mirror" hygrometer.

My pending application describes a new type of primary optical hygrometer in which the mirror is heated instead of chilled. It is analogous to the cold mirror hygrometer but it is highly superior because of its smaller size and lower power consumption. However, in spite of its general excellence for many applications, neither it nor the cold mirror hygrometer is suited for the overall ultra-miniaturization found in ICs (integrated circuits) or VLSICs (very large scale integrated circuits). This is because substantial but variable cooling or heating of the integrated circuits which are intimately associated with the operation of the sensor mirror introduces complex non-linearity problems and radiation effects.

In response to the urgent need for miniature military radiosondes, humidity sensors to incorporate within VLSIC "packages," and other critical applications, humidity sensors have been developed by others. These depend on the change of electrical capacitance of various dielectric materials as the humidity over the materials varies. However, these sensors are of the secondary type in which the moisture (which causes the dielectric constant change in the dielectric material) is sorbed in a non-linear and non-reproducible way which shifts with time. Thus, if the sensor is accessible (as in a radiosonde) a very difficult field standardization of the sensor must be attempted before sending the balloon aloft. If the sensor is sealed into a VLSIC package to monitor its interior, there is no way to check and compensate for the sensor's drift. Thus, what has been sorely needed is a capacitance-type, primary standard humidity device which (a) operates at ambient temperature, (b) has a sensor which is invariant, and (c) has a mode for quickly checking for electronic circuit problems.

The sensors of the present invention are unusual in that the humidity-responsive sensors generate concurrent primary optical-type and primary capacitance-type signals. Even well designed and properly manufactured integrated circuits can abruptly develop circuit problems. These can result in false humidity readouts even though the capacitance/humidity changes of these sensors are invariant. With these new sensors an ongoing monitoring of the soundness of the electronics of devices which utilize the snesors in the capacitance mode can be readily provided by simultaneously optically monitoring the sensor. For example, providing a small window in one of the capacitance electrodes will allow the sensor film to be seen. It will show a dark field/bright field shift every time the gases over the sensor reach a known, precise, invariant humidity. A readout of this humidity should appear concurrently, of course, on the display screen of the capacitance meter. If desired, for convenience the same sensor material as is used between the capacitance electrodes can be optically displayed elsewhere in the systemm which transports the gas across the capacitance electrodes/sensor film for measurement.

The use of spatially separated dual sensors of the same composition, one sensing optically and the other capacitively, has the additional merit of allowing one to readily optimize the thickness of each for its particular function. Thus, an optical-type, humidity-/responsive sensor might be coated at a thickness of about 0.01 mm. in order to secure a brilliant readout. However, a capacitance-type sensor might be coated more thinly since the capacitance and the sensitivity of an "electrode/humidity-responsive dielectric composition/electrode" triad increases, as the thickness of the dielectric composition decreases. If dual sensors are not convenient, a very small area of a very thinly coated sensor film being monitored capacitively may be of greater thickness so that when scanned optically a brilliant optical readout results.

In my U.S. Pat. Nos. 3,776,038, 4,166,891 and 4,175,207 I describe optical type, humidity-responsive devices of great utility which cover the middle range of relative humidity. However, in computer science, electronics in general and other specialized fields, the extreme humidity ranges are of special importance because of the corrosive effect of water condensing in equipment at very high humidities and static sparks (electrostatic discharges) damaging microelectronics at very low humidities. Both in electronic capacitive-responsive devices and in direct optical readout devices the sensors of the new technology allow covering the relative humidity (RH) range down to 15% and below and 85% and above. Thus, their primary, invariant qualities allow precise monitoring of ranges which until now have been notorious for generating badly drifting signals since the sorption processes used by ordinary hygrometers become increasingly erratic at very high and very low humidities.

SUMMARY OF THE INVENTION

The present invention provides novel chemical compositions for use in primary standard, optical/capacitance-type or optical-type or capacitance-type hygrometric devices. It also provides methods for using these compositions as sensors for the precise measurement of the humidity of gases as well as the apparatus.

As a result of extensive research I have discovered novel chemical compounds which function in a new and unexpected way to indicate the ambient humidity through changes in optical properties and/or electrical capacitance. I have also discovered what I term "lattice modifiers", novel compounds to extend the humidity ranges covered by the basic sensors. Further, I have devised compounding methods for the sensors and sensors/lattice modifiers which make them suitable for production coating and utilization in a variety of hygrometers, controls, and humidity-sensing devices.

The devices and methods of the new hygrometry allow many variations on the primary requirements. For example, if the sensors are to be operated in the optical mode, light sources such as LEDs, tungsten lamps, neon lamps, etc. can be used with a variety of light detecting means such as photo-transistors, phoyto-SCRs, photo-diodes, photo-resistor cells, the human eye, etc. If amplification of the optical change is desired, circular-type polarizers can be used with reflection systems and crossed-linear type polarizers can be used with transmission systems. If the sensors are to be operated in the electrical capacitance mode, electrical power of various voltages can be used. Frequencies used may range from direct current to radio frequencies, though I have found a 3-10 volt signal at 1000 Hz a convenient source. Various capacitance measuring devices of good accuracy are readily available, the meters widely used for measuring the capacitance of capacitors proving quite suitable. If desired, the sensor can be made an integral part of a capacitance-sensitive IC. Thus, a humidity-induced change in the dielectric constant of the sensor of the IC device produces a proportional change in the output of the IC device.

The sensors used for capacitance mode sensing can be of widely varying area and thickness depending on the electronics used for indicating and/or recording and the applications of the device. Electrode spacing can be varied, and electrode materials of various types can be used so long as they are not corroded by the humid gases being sampled or by the sensor compounds.

A number of modes of placing electrodes have been used by workers in this field and most of these work nicely. These include co-planar interdigitated electrodes, parallel plate electrodes, and co-planar series connected electrodes. Opposed, planar electrodes, with the upper electrode perforated so that the monitored gas reaches the sensor film which is coated onto the lower electrode work well. To prevent electrical conduction through the sensor compound, the upper or lower electrode can be coated with a very thin film of insulating polymer, or an air space can be left between the sensor film and the upper, perforated electrode.

The use of co-planar, polymer insulated, interdigitated electrodes coated with the humidity sensing material also can be used. Often, a gas permeable, light weight secondary electrode is floated on the surface of the sensor film over the interdigitated electrodes so as to secure a higher electrode area exposure than can be secured from only the edges of interdigitated electrodes. If desired, two or more sensor films covering contiguous humidity ranges can be applied to the electrode in a coplanar, contiguous manner so as to cover an exceptionally broad humidity range. Or, an electrode bearing a sensor film covering one humidity range can be covered with a humidity permeable, diffusion-blocking polymer film and then coated with a sensor film covering a contiguous humidity range. The second electrode is then located appropriately above the multiple-sensor layer film.

The chemical compositions, which of themselves sense the change in water vapor pressure, are birefringent, translucent, and anisotropic at a first water vapor pressure and temperature, but non-birefringent, optically clear, and isotropic at a second vapor pressure and temperaturer. As was noted, the optical changes which accompany these phase changes may be amplified by passing the light beam through a polarizer and passing the polarized beam through the composition and then through an analyzer to a detector.

Some compositions, when compounded appropriately, exhibit abrupt and large increases in their dielectric constant coincident with the optical changes which occur at the phase shift point, the middle section of the curve being substantially linear. Others show a large and precisely linear change in dielectric constant over many decades of relative humidity (RH), but the optical shift occurs at a precise point within the range. Thus, though non-linearity may be encountered at the very ends of such curves, the linear sections are very large and so are readily used for effective commercial and scientific read-out and control. By noting the capacitance readout from a prestandardized combination optical/capacitance hygrometric device at the moment of optically indicated phase shift (when the system changes from isotropic to birefringene), any drift in the electronics of the device can be immediately detected since the sensor's phase shift point is invariant.

If it is desired to eliminate polarizer amplifiers because of their cost, sensor substrates can be shaped so that internal reflection within the substrate and optical coupling of the birefringent sensor to the substrate generate excellent optical signals at the sensor's trigger points.

THE DRAWINGS

Figure 8A:
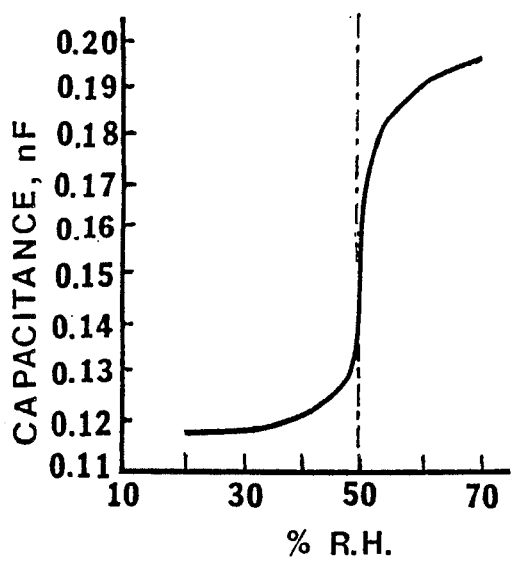

FIG. 8a is a capacitance vs. RH curve for an alkali metal complex humidity sensor much as claimed in U.S. Pat. No. 4,166,891.

Figure 8B:
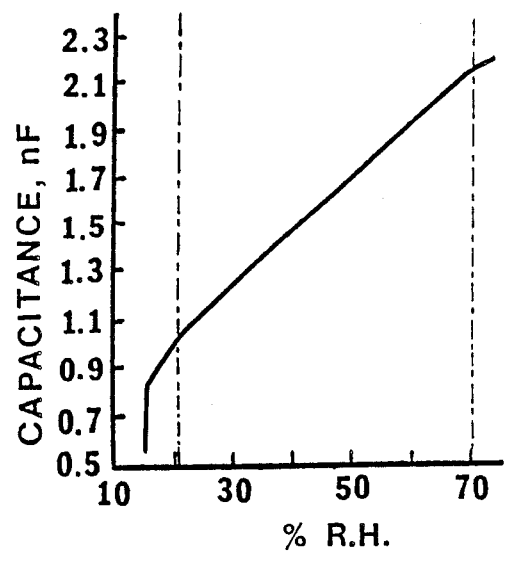

FIG. 8b is a capacitance vs. RH curve for the huidity sensor cesium benzoylpropionate.

Figure 8C:
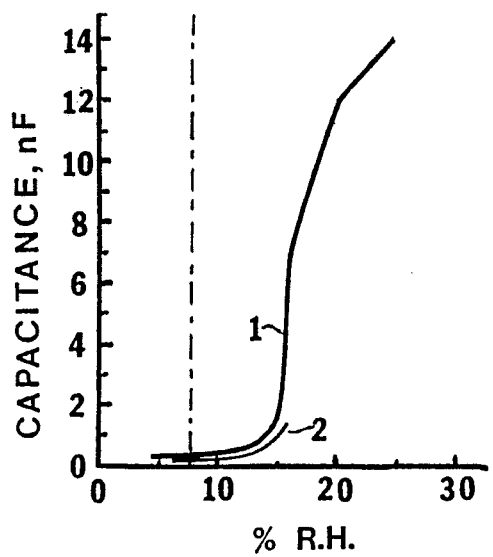
Figure 8D:
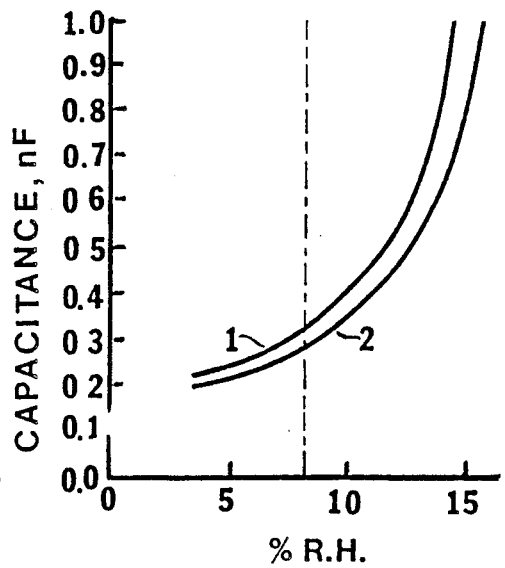

FIG. 8c are capacitance vs. RH curves before and after thermal processing for a humidity sensor comprising calcium chloride compounded with silica; and FIG. 8d is an enlarged section of the capacitance vs. RH curves of FIG. 8c.

DETAILED DESCRIPTION OF THE INVENTION

In my U.S. Pat. Nos. 3,776,038, 4,166,891, and 4,175,207 I claim sensor compositions which undergo two phase shifts, namely, from an isotropic solid to an anisotropic solid and then, at higher humidities, from an anisotropic solid to an isotropic solution (usually used in a gelled state). This can be summarized thus:

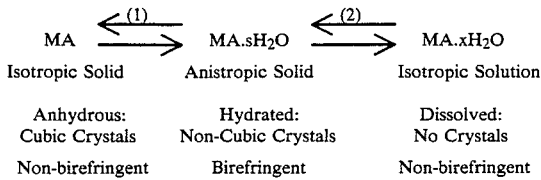

Though this dual signalling has worked well for direct readout devices, electronic devices can be more simply designed if the sensor undergoes only an unambiguous "on/off" or "birefringent/non/-birefringent" shift. The novel sensors of the present inventoin undergo only phase shift (2) shown above. This is a reversible shift between an anisotropic (birefringent) crystal and an isotropic solution (non-birefringent).

Figure 1:
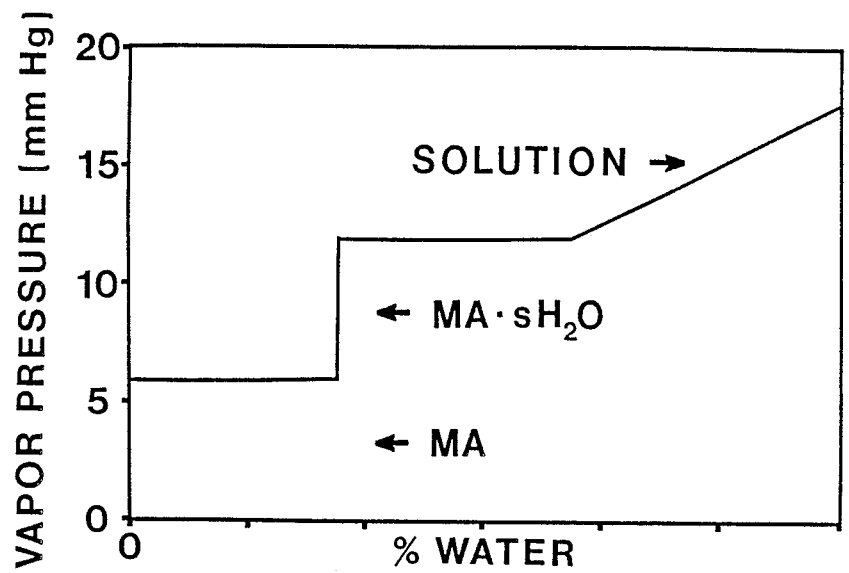
FIG. 1 is a vapor pressure curve for hydrates of a typical salt, MA (where M is a metal cation and A is an acid radical), at 20° C.

These mechanisms can be described simply with reference to FIG. 1. If we increase the vapor pressure of water in the presence of the sensor salt MA, no reaction occurs until a critical vapor pressure is reached. Then a hydrate, MA.sH$_2$O, with s representing a specific molecular ratio, starts to form. Any attempt to increase the water vapor pressure is then countered by the formation of more hydrate until all of the MA has reacted. Only then can the water vapor pressure increase. Because of the relatively easy removal or addition of water, the hydrate water is specifically indicated as H$_2$O, though it is chemically bound.

If the water vapor pressure increases still more, the hydrate deliquesces. That is, the compound removes water from the surrounding atmosphere to form an isotropic solution. All soluble salts are deliquescent when the partial pressure of the water vapor in the atmosphere exceeds the water vapor pressure of their saturated solution. Though the birefringent, anisotropic sensor salt in the phase equilibria shown above (and illustrated in FIG. 1) is hydrated (MA.sH$_2$O), birefringent salts can also be anhydrous. In such a case, the anhydrous birefrigent salt directly deliquesces to a non-birefringent, isotropic solution. Once all of the salt has dissolved, a further increase of water vapor pressure brings dilution of the saturated solution. This technology uses the crystal/solution phase shift point for optical signalling because it occurs at a very precise and reproducible humidity and temperature. The salts may be gelled so that the sensor passes from opalescent, anisotropic films to clear, isotropic gels at the optical signalling point.

Figure 2:
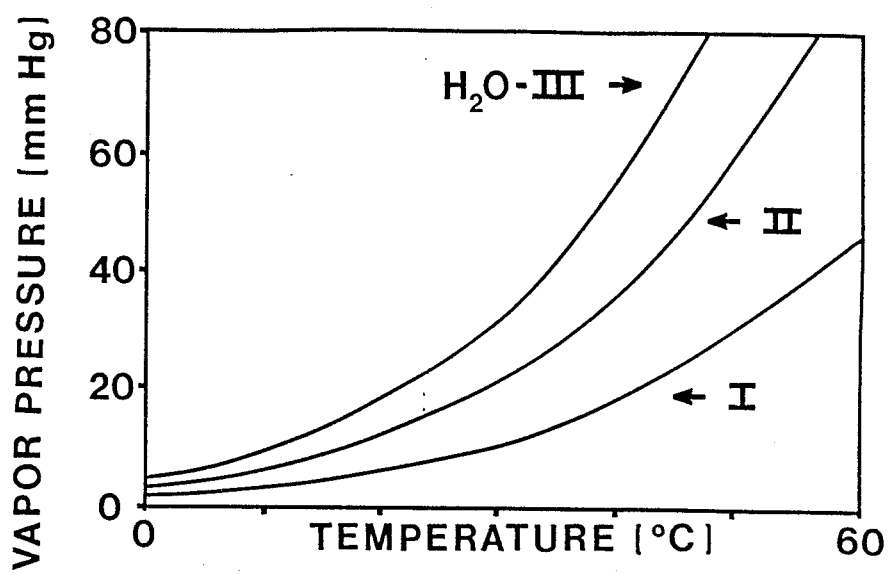
FIG. 2 shows typical vapor pressure temperature curves for water and hydrates of a salt, MA.

FIG. 2 shows the effect of temperature on the equilibrium of the system described above. On each line the phases stable in the adjacent regions are in equilibrium. The stable crystal or liquid phases are: Below I, anhydrous; I–II, MA.sH$_2$O; II–III, solution.

As noted earlier, the sensors of this technology undergo both optical and dielectric constant changes of great potential utility. These changed may be utilized separately or together. Utilizing optical changes only will be considered first. As notes, this technology uses sensing compounds which undergo isotropic/anisotropic changes at the phase shift point or "trigger" point. In the isotropic form the optical properties of the solution are the same in every direction. The phase shift forms anisotropic crystals which have optical properties which vary with direction. In particular, the crystals have at least two indices of refraction and so are birefringent. Further, the shift from the clarity of the liquid phase to the opalescence of the crystal phase may be amplified readily with polarizers.

Figure 3:
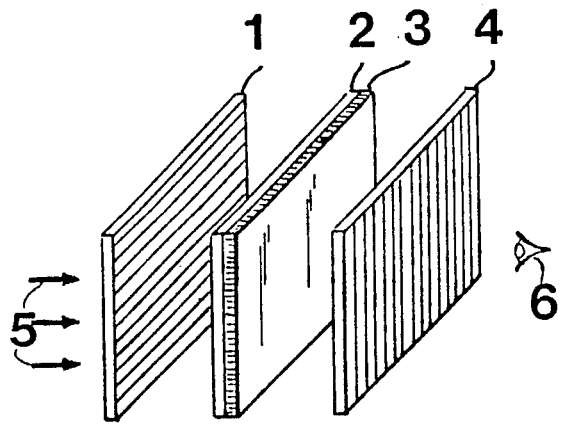
FIG. 3 is a schematic view of an optical-type transmission system.

In a representative transmission-type embodiment of the optical mode of the present invention shown in FIG. 3, a light beam from light source 5 which may be a window, a tungsten lamp, an LED, etc. passes through polarizer 1 where the light beam is polarized. The beam then passes through transparent or translucent substrate 2 which may be glass or some isotropic plastic such as cellulose triacetate, on which is deposited sensor layer 3. The beam passing through 2 and 3 then encounters analyzer 4 whose polarizing axis is usually at right angles to the polarizing axis of 1 so as to result in what is generally termed "dark field."

If the coating 3 on substrate 2 is in its non-birefringent mode, little light passes through analyzer 4 and the system appears "dark field" to viewer 6. However, if the humidity changes sufficiently, coating 3 becomes birefringent. When a light beam enters a birefringent or, as it it is sometimes called, double refracting material, it is divided into two components, one defined as an extraordinary ray and the other as an oridnary ray, each vibrating in a direction at right angles to the other and traversing the birefringent material with a different velocity to thereby introduce a phase difference there between. As said beam is therby resolved into two components, one of which is retarded with respect to the other, said beam is generally referred to as being elliptically polarized. The two components emerging from the birefringent material and entering the second sheet of polarizing material 4 are resolved into one plane-polarized beam again. But a phase difference has been introduced between the two parts of this same beam, and so the necessary conditions for interference are present. With a white light source brilliant colors will emerge from analyzer 4 if the coating consists of large crystals. However, when the crystals are very small there is a mixing of colors and the crystal mass appears white. But in either case the field which was previously a blue-black passing very little light now glows brilliantly.

Figure 4:
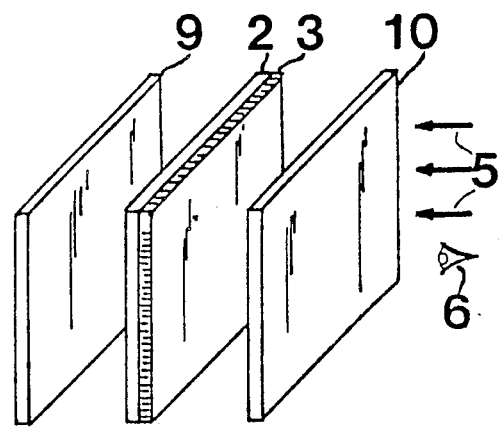
FIG. 4 is a schematic view of an optical-type reflection system.

FIG. 4 typifies a reflection-type system in which light beams from a source 5 pass through a circular-type polarizer 10 where they are circularly polarized. They then pass through the sensor layer 3 coated onto substrate 2 to the polarization conserving mirror 9. When the coating 3 is non-birefringent, no light will be reflected back through 10 because the circular polarizer has polarized the beam to a "right-handed" or "left-handed" helix form which cannot pass back through the circular polarizer 10. When coating 3 becomes birefringent, the polarization form of the light that is reflected from the mirror is altered and the returning light passes through the polarizer 10.

Figure 5:
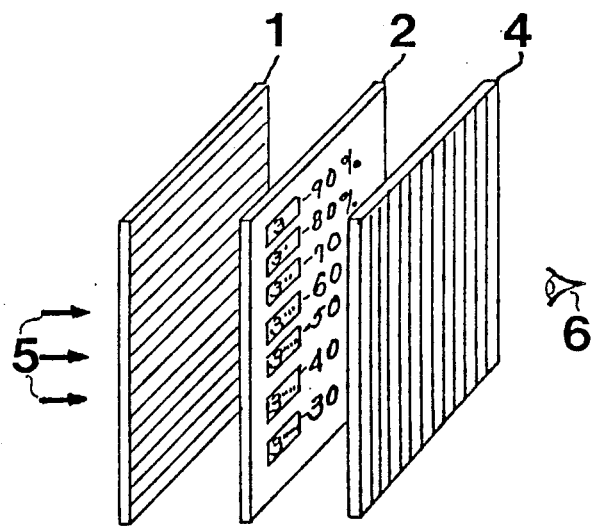
FIG. 5 is a schematic view of an optical-type transmission system using sequential RH series plaques.

FIG. 5 also represents a transmission-type embodiment of the optical mode but it is one in which a graded series of RH sensors are displayed so as to cover a particular humidity range. It is similar to FIG. 3 but instead of a single coating 3 on substrate 2, the graded series 3, 3' 3'', etc. are applied in discrete areas on the substrate.

Figure 6:
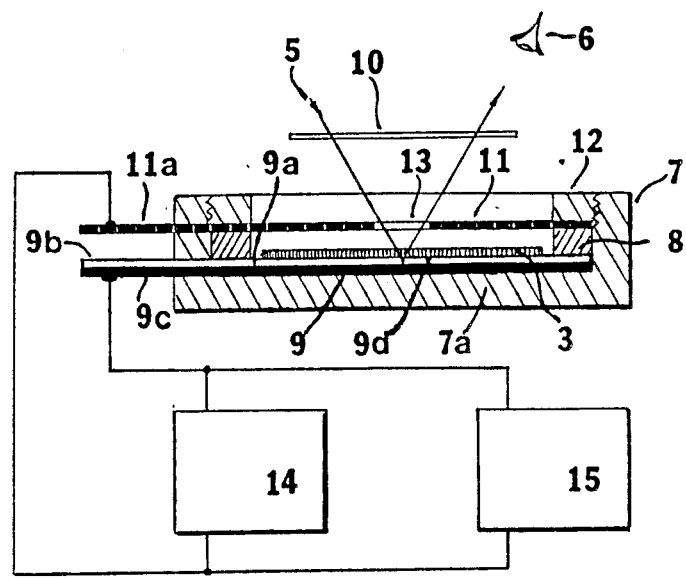
FIG. 6 is a section of a capacitance-type humidity sensing device.

FIg. 6 represents a section of a typical embodiment of the capacitance/optical mode of the technology. 7 is a side slotted, annular holder made of an electrically insulating polymer of low water sorption character such as Teflon into which a threaded retaining ring of Teflon 12 screws. 9 is a flat, polished circular metal mirror electrode coated on the upper mirror side 9a with a thin, isotropic electrically insulating film such as the insulating polymer heretofore referred to or an aluminum oxide as is identified in FIG. 6 at 9b placed upon the base 7a of holder 7 and which has a long narrow tab 9c extending through the side of slotted holder 7. 3 is a humidity-responsive sensor coating of the present invention coated on the middle of the upper surface 9d of mirror 9. 8 is an annular spacing ring of an electrically insulating, low water sorption polymer such as Teflon machined to a precise thickness. 11 is a flat, perforated, circular, metal electrode having a long, narrow tab 11a (similar to that of 9) which extends thorugh the side of the slotted holder 7. To monitor the state of the sensor film, a light beam from light source 5 passes through circular-type polarizer 10 where the beam is circularly polarized. Then the beam passes through the circular aperture 13 in perforated metal electrode 11 and then, as in FIG. 4, through the sensor layer 3 coated onto mirror substrate 9. As explained before, reflected light from light mirror 9 emerges from the aperture 13 and passes through the polarizer 10 to be perceived by the viewer or by a photo-responsive device at the moment the sensor layer 3 becomes birefringent. Electrodes 9 and 11, of course, are connected to a suitable capacitance meter 14 which may be calibrated in percent RH rather than picofarads. Voltage is applied to the electrodes by voltage source 15. Prior determination of the primary, inherent "trigger point" or optical phase change point of the sensor material used allows precise checking against the readout shown by the capacitance meter at the moment of optical shift. Perforated electrode 11 may have its viewing port and ventilation holes closed with a very thin coating of a polymer highly permeable to water vapor (such as cellulose acetate butyrate) if it is desired that the cell be impermeable to liquid water. In such a case the emerging electrode tabs are sealed with an RTV silicone compound. A polymer coating 0.002 mm. or less is suitable on the top electrode.

Figure 7:
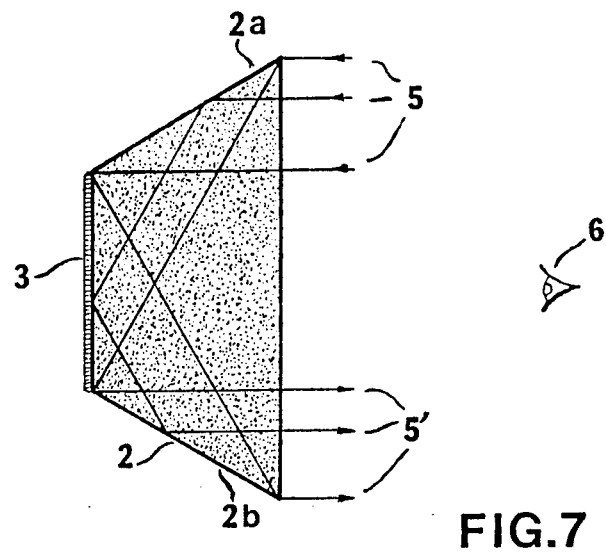
FIG. 7 is a section of an optical-type reflection system not requiring polarizer amplification.

FIG. 7 is a cross section of a trapezoid-shaped bar of transparent glass or of a plastic such as polymethyl methacrylate. This has been discovered to generate excellent optical signals without the use of polarizer amplifiers when used with the humidity sensors of the present invention. The device consists of a bar shaped substrate 2 of suitable length to carry one or more plaques of sensor coating 3 on its back side. Light beams form light source 5 enter the trapezoidally shaped bar whose angles have been chosen to cause total reflection to occur to the beams which encounter the two non-parallel sides 2a, 2b of the trapezoid. To illustrate this reflection, beams 5 are shown entering the structure, being internaly reflected, and exiting as beam 5'. Since the trapezoid is symmetrical, this reflection occurs on both sides.

Unexpectedly, the sensors of the present invention have been found to optically couple with the trapezoidally-shaped substrate when the sensors are in their birefringent, opalescent phase. The viewer 6 perceives only a faint, opalescence when looking through the bar 2 and the coating 3 in the center zone (between the lines of beams 5 and 5'). However, the two edge zones, which are mirror reflections of coating 3, appear brilliantly white. When sensor coating 3 shifts to isotropic and transparent, the two edge zones reflecting that sensor abruptly become silver, giving a dramatic signal shift.

Many variations of this structure are possible. The front center zone can be used to carry a scale showing the trigger humidities of a graded series of sensor plaques on the back side. Instead of a trapezoidal shape, a semi-circular or even half of an annular shape can be used. In the case of the trapezoidal shapes, it is necessary to select trapezoid angles which will cause total internal reflection within the particular transparent material used. The "critical angle" can be readily calculated from the index of refraction of the desired substrate, of course. Light beams also can be passed into either end of such bars to illuminate sensors coated on the back. If desired, the readout from these systems, can be further enhanced by viewing the front face through a circular-type polarizer parallel with it.

If a trapezoidal shape is used, the humidity-sensing compositions are applied only to the flat back of the device, in one or more stripes of any desirable width, optimally extending from one edge to the other whatever the width selected for the back of the trapezoid. Though such stripes can be carried up the non-parallel sides of the trapezoid, only a very small increase in signal contrast results and the effort is not warranted.

If a semicircular or semiannular shape is coated with one or more humidity-sensing compositions, the stripes as before are parallel and of any convenient width. For convenience in coating, the stripes may extend from one front edge to the other front edge, spanning the entire 180° of the semicircle. However, the length of the stripe may be substantially shortened while still generating a good optical signal. Generally, it is desirable that at least 25% of the semicircular arc be coated and the coating should be of approximately equal length either side of the centerline.

FIG. 8a is a capacitance vs. RH curve of a sodium/potassium mixed crystal salt complex such as is described in claim 13 of my U.S. Pat. No. 4,166,891. It has an optical trigger point of 50% RH (indicated by the vertical dashed line at 50%). Magnesium compounds are an essental stabilizing component in this complex of the alkali metal salts of 3,3',4,4' benzophenonetetracarboxylic acid. As noted elsewhere, magnesium compounds cannot be used in conjunction wth the complexing of the alkali metal organic salts of the present invention since they cause decomposition. The huge shift in the dielectric constant of the complex, as indicated by the almost vertical shape of the capacitance vs. RH curve, occurs concurrently at the optical trigger point. This curve was developed using the sensor fixture illustrated in FIG. 6, as were the other curves shown in the FIG. 8 series.

FIG. 8b is a capacitance vs RH curve of the pure organic salt, cesium benzoylpropionate, whose preparation is described in detail further on. In this typical example, the large, linear change in the dielectric constant extends over almost five decades of relative humidity as indicated by the vertical, dashed lines. Homologs of this compound extend the range covered to very high humidities and lattice modifiers extend the range to very low humidities. As noted elsewhere, the optical shift for each compound occurs at a very precise humidity along its capacitance vs. humidity curve.

FIG. 8c shows capacitance vs. RH curves of the inorganic salt, calcium chloride, compounded with a high surface area silica. As a matter of interest, curve 1 shows both the high RH as well as the low RH portions of the curve. However, as explained in detail further on, this sensor is an example of a special type used for monitoring low humidities under very rigorous conditions. Thus, curve 2, which is a capacitance vs. RH curve developed with the identical sensor after a 500° C. thermal porcessing, was tested only at lower humidities since this is the range of interest.

The vertical dashed line marks the 2000 parts per million by volume of water vapor which the Military has established as the limit of internal water vapor content for high reliability microcircuits packaged in hermetically sealed ceramic packages. This is equivalent to approximately 8% RH at 20° C. and it is in this lower range that a sensor such as this is used for monitoring the atmosphere of sealed packages.

FIG. 8d shows the same two capacitances vs. RH curves 1 and 2 as shown in FIG. 8c, but the scales are expanded to cover only the capacitance and RH ranges of interest. It shows the capacitance readouts which can be readily secured in greater detail than can be seen in the curves of FIG. 8c.

Curves 1 and 2, FIG. 8d, vary by about 1.5% RH since, as explained elsewhere, the test assembly shown in FIG. 6 was not designed to be fired at 500° C. In particular, after developing curve 1, the assembly was disassembled, the electrode bearing the sensor film was fired at 500° C., cooled, and reinstalled in the assembly for determining curve 2. Capacitance test devices designed to be assembled and disassembled are manufactured to very close tolerance because of the large change in capacitance with small change in electrode clearance. The test device of FIG. 6 is not of this precision. However, the FIG. 6 device, once assembled, has repetitively generated such curves as are shown in FIG. 8a and FIG. 8b. Curves such as 1 and 2 of FIG. 8c and FIG. 8d, though already acceptable by present commercial standards, are expected to fall into very close clusters when sensors such as are described here are installed in electrode assemblies designed for high temperature processing.

Turning to the chemical compounds which I have discovered exhibit these concurrent optical and dielectric constant changes, I have found them remarkable for their sensitivity to very small changes in the humidity of gases in contact with them. This is believed to be due to the unusually propitious balance of forces within the molecules. Thus, as the ambient humidity varies and they shift phase from an isotropic solution to anisotropic crystals, they do not form the highly organized, tightly bound type of crystal which dissolves with difficulty as the humidity varies. Nevertheless, the intermolecular forces among the dissolved molecules are strong enough to eliminate any tendency toward supersaturation when water leaves the system.

There is an explanation for this remarkable behavior. Though I do not wish to be bound by theory, it is believed that the salts of the present invention form lyotropic liquid crystals as solvent water leaves their isotropic solutions. Though a good deal of work has been done on "thermotropic" liquid crystals (the type used in "liquid crystal" thermometers and electronic "liquid crystal" displays) and which are entirely different, little work has been done with lyotropic liquid crystals. The common bond between the two categories is that in each case the sensing molecules shift between an isotropic liquid state and a "liquid crystal" state. The term "liquid crystal" is used to describe a state in which a good deal of molecular order is present as compared with the liquid state. However, the molecules are not as organized as they are in the solid where constituent molecules execute small vibrations about firmly fixed lattice positions but cannot rotate. The ordinary liquid state, of course, is characterized by relatively unhindered molecular rotation and no long-range order.

First turning to the chemistry of these sensors in a general way, the sensory molecules are amphiphilic. That is, they are characterized by possessing an organic ring structure that is water insoluble (hydrophobic) and a side chain with a polar head (ionic) which dissolves readily in water (hydrophilic). However, I theorize that under suitable conditions the cation of the side chain bonds to the oxygen of the benzoyl group to form a novel polar ring complex which is highly susceptible to hydration because of its ionic nature. This compact multi-ring structure which forms is believed to be unusually suitable for the formation of lyotropic liquid crystals. It is also a structure offering excellent stability to heat and ultraviolet light.

I have found that a number of molecular structural modifications can be made and still preserve the essential humidity-response of the sensors of the present invention. However, the alkali metal salts of 3-benzoylpropionic acid, $C_6H_5COCH_2CH_2CO_2H$, or the alkali metal salts of the ring-substituted benzolypropionic acids have proven of exceptional utility. The alkali metals which are useful include lithium, sodium, potassium, rubidium, and cesium since the different metals form salts which trigger or undergo phase shifts at different humidities. Further, so as to prepare formulations which trigger at intermediate humidities, mixtures or so-called mixed crystals can be formed by cross-mixing the salts of the different alkali metals.

Among the various substituent groups which are useful in modifying the phenyl ring, I have found that alkyl groups create compounds whose alkali metal salts trigger at humidities far higher than do those of the non-alkylated benzoylpropionic acid. For example, the compounded potassium salt of 3-benzoylpropionic acid triggers at about 53% RH at 20° C. but the compounded potassium salt of 3-(4-ethylbenzoyl) propionic acid, $C_2H_5C_6H_4COCH_2CH_2CO_2H$, triggers at 83% RH at 20° C. A greater degree of alkylation raises the trigger point of the alkali metal salts still higher.

The lowest humidity which the compounded (but non-modified) alkali metal salts of 3-benzoylpropionic acid will sense is 35% RH at 20° C., the trigger point of the cesium salt. However, it is desirable to sense much lower humidities. I have discovered a new class of compounds which meet this need, and I term them "lattice modifiers" since they are believed to function by profoundly altering the intermolecular forces within the liquid crystal lattice. Thus, the prime, sensing molecules (for example those of cesium benzoylpropionate) do not associate at their "natural" trigger humidities but at much lower humidities when mixed with these lattice modifiers.

These modifiers are chain-like with polar heads (ionic) and they closely resemble the side chain attached to the phenyl group of prime sensing salts such as cesium benzoylpropionate, $C_6H_5COCH_2CH_2CO_2Cs$, in which $-COCH_2CH_2CO_2Cs$ is the side chain. For example, an effective lattice modifier, cesium hydroxybutyrate, $H_2COHCHCH_2CH_2CO_2Cs$, is the same as cesium benzoylpropionate's side chain except that the keto group (C=O) has been replaced by an hydroxyl group (C—OH). As before, it is believed that the chain forms a ring structure in which the Cs bonds to the oxygen of the hydroxyl group. It is theorized that these molecular "separators" or spacers make it increasingly difficult for the prime sensing molecules to assemble into liquid crystal signalling "swarms" or arrays. The reduction of the RH trigger point is a linear function of the quantity of lattice modifier added, and the modifiers are quite potent. By such a method the trigger point can be reduced below 15% RH at 20° C. while preserving the full brilliance of readout and the sensitivity to small humidity changes.

What I term "compounding" of the prime sensor salts and their lattice modifiers is also of great value, though for many applications the sensor salts (with or without modifiers) can be used as uncompounded solutions. When they are used in an uncompounded form, it is desirable to limit the area and depth of each incremental sensor salt deposit so that surface tension prevents running or draining of the deliquesced liquid which it forms at high relative humidities. This is especially true if the sensors are to be used in the vertical position. Then the solution can be applied in small droplets. If desired, the surface tension of the substrate area between droplets can be readily raised by crosshatching the substrate with narrow line deposits of water repellent materials such as fluoropolymers.

Compounding of the sensor salts offers various benefits. For example, equalizing the viscosity and surface tension of 16 or more sensor solutions before simultaneously coating a graded RH series onto a moving substrate greatly facilitates the process. Once applied, proper compounding creates chemical complexes which signal brilliantly, shifting from a birefringent liquid crystal state to an isotropic gelled state, a form which never becomes fluid enough to drip or run at high humidities.

In my U.S. Pat. No. 4,166,891 I describe polymers and certain metals and borates which create complexes of great utility when used with those chemical sensors. In the claims covering those complexes I particularly specify magnesium, $Mg^{++}$, because it is essential to the long term stability of those complexes. However, I have discovered that the chemistry of the present sensor compounds is entirely different from that encountered with the alkali salts of 3,3'4,4' benzophenone tetracarboxylate, the sensors of the earlier invention. With the new sensors the inclusion of magnesium salts brings immediate formation of insoluble complexes which make the composition useless. Thus, though there appear to be similarities between the complexing of the benzophenone sensors and the salts of the present invention, the essential chemistry of the complexing is entirely different as is confirmed by the magnesium reaction.

As before, I have found that water soluble, organic polymers containing repetitive oxygen-bearing groups including the hydroxyl, the carboxyl, the sulfonic acid group, or mixtures of them repetitively present along a substantially linear chain are useful compounding ingredients. Examples of these polymers, which are preferably solid and which have proven effective, are as follows: carboxyl group-poly(methyl vinyl ether/maleic anhydride), poly(styrene/maleic anhydride), polyacrylic acid; sulfonic acid group-polyvinyl sulfonic acid; methoxy group-methoxy cellulose; polyether group-polyethylene oxide; polyamide group-poly(vinylpyrrolidone). The carboxyl and sulfonic acid groups must be neutralized with an appropriate alkali metal compound before use so that the system is neutral or slightly basic. Some of these polymers are modified in various ways during manufacture. For example, polyacrylic acid is often modified by inclusion of methacrylic acid and/or crosslinking agents during manufacture.

The molecular weights of the polymers in general are not critical so long as the polymers form stable, water solutions of appropriate viscosity. Usually, from about 2% to 8% of the polymer in a coating solution containing 8% by weight of sensor salt contributes good rheological properties to the coating solution.

Though I do not wish to be bound by theory, it is thought that the metal cations which I have found effective with the present chemical sensors coordinate with the oxygen of the polymers to form elaborate network structures. The metal ions which coordinate with the polymers and with the sensors of the new invention to form appropriately complexed compositions are $Cu^{++}$, $Ni^{++}$, $Co^{++}$, $Mn^{++}$, $Al^{+++}$, $Zn^{++}$, and $Cr^{+++}$. Since the salts must be appropriately soluble for reaction, the nitrate, chloride, acetate, and sulfate typify useful anions. Usually about 5 mol percent of the metals present in an alkali metal benzoylpropionate/polyvalent metal salt mixture must be of the polyvalent metal salt for good complexing, though as little as 0.4 mol percent may prove adequate.

Besides the heavy metal cations which form such useful networks with the polymers to enhance viscosity in the solution and in the deliquesced film, I have found that the boron introduced as a borate is a most effective agent to gel the viscous films which form on evaporation of water from a sensor salt/polymer/polyvalent heavy metal salt solution. Alkali metal borates form complex ring structures in water, and it is believed that the oxygenated polymers and polyvalent cations react with these rings to form elaborate stable networks which can readily swell at high humidities but which are so crosslinked that they cannot dissolve.

I have found that about two mol percent of borate ion on the basis of the metals present in the sensor salts/polyvalent metal salts/polymers blend usually prevents any dripping even at 90% RH and 50° C. However, as little as 0.25 mol percent can prove adequate and as much as 10 mol percent can prove desirable when very high humidities are expected. The strength of the complexing of these components, namely, the alkali metal sensor salts and borates, the heavy metal salts, and the polymers is demonstrated by the brilliantly clear solutions which form while at the same time the non-flowing films which they form retain their integrity at high temperatures and humidities.

Finely divided inorganic compounds having little or no birefringence and possessing a high surface area also can be used advantageously in compounding the prime sensor salts and their lattice and modifiers. Since the dielectric constants of the inorganic compounds are quite different from those of organic polymers which are also most useful in compounding, they offer a most convenient mode of modifying the electrical characteristics of the sensor system while securing rheological properties in the sensor solutions which make them suitable for successful coating.

Precipitated and pyrogenic silica, diatomaceous earth, and pyrogenic aluminum oxide typify oxides which are commercially available having surface areas as high as 50-200 sq. meters/gram. From 0.5 to 4.0% by weight of such materials can be readily dispersed in aqueous solutions of prime sensor salts (containing lattice modifiers where desired) which contain from 10-50% of sensor salts by weight. The pH of the suspension is then adjusted to the 7.5-8.5 range using the appropriate alkali metal hydroxide. Such dispersions coat well and dry to films of great sensitivity to humidity changes and free of drainage problems.

Pyrogenic aluminum oxide and silica are of exceptional value because by empirically adjusting the ratio of one oxide to the other the viscosity of a particular dispersion can be adjusted over a much wider range than can be secured with either alone.

I have found that there is still another type of compounding component which is essential for good signalling with lyotropic liquid crystals. I term such materials "lattice stabilizers," and they stabilize the liquid so that the liquid crystals form but one type of structure. Solid crystals often can form more than one well-defined structure, and so there is often a problem with stabilizing a system so that only the desired crystal type forms. Liquid crystals, however, are much more complex since the intermolecular bonds are weaker. Thus, many subtle, undesirable variations on a particular, desired crystal structure can occur in an uncontrolled system because of temperature variations, variations in the rate of crystal formations etc. However, I have discovered certain additives which are believed to create a kind of "reference lattice structure" within the lyotropic liquid crystal system so that the sensor molecules always assemble into crystals in such a way as to generate the same optical and dielectric constant readouts. This reference lattice structure is invisible but potent in its organizing power.

One type of lattice stabilizer consists of aryl hydrocarbons of low vapor pressure which dissolve in the sensor salt/polymer/water system to form organizing complexes of still lower vapor pressure. Examples of hydrocarbons which perform well include Monsanto's HB40, which is a partially hydrogenated terphenyl which also contains about 40% of terphenyl. 1,1-di(ortho-xylyl)ethane, 1,2,3, 4 tetramethylbenzene, 1,2,4,5 tetramethylbenzene, 1,2,3,5 tetramethylbenzene, 1,2,3,4,5 pentamethylbenzene, and cyclohexylbezene are also hydrocarbons which bring about consistent organization of the liquid crystals, increase the brightness of optical readout, and minimize hysteresis. Hysteresis is the difference in the humidity level at which triggering occurs when the humidity is rising compared to that met when the humidity is falling. Typically, from 1 to 3% of the hydrocarbon on the basis of contained solids is very effective.

Another type of potent lattice stabilizer consists of certain surface active agents in which a stable fluorocarbon tail, $F_3C(CF_2CF_2...)$ is attached to a water-solubilizing group, X. The alkali metal perfluoroalkyl sulfonates, carboxylates, and acid phosphates comprise the compounds which are effective. The perfluoroalkyl group varies in length among different compounds and manufacturers but typically includes 3 to 8 carbons. A small concentration of agent is usually quite effective. From 0.1% to 0.3% on the basis of contained solids is usually quite effective.

Having overviewed the various components of these complex but remarkably effective and useful systems, it is helpful to consider the components in greater detail. Since the salts of benzoylpropionic acid and its homologs and analogs comprise the central sensors of these systems, the synthesis of benzoylpropionic acid is most useful to consider. Typically, the various acids from which effective sensor salts can be made can be synthesized by using the same method or a variation on the method which would be obvious to one skilled in the art. Usually, a variation in concentration of reactants, temperature of reaction, or choice of solvent will produce a satisfactory yield of the desired acid in good purity.

The Friedel and Crafts reaction is the one most useful for preparation. The reaction of succinic anhydride with benzene or the desired alkylated or arylated benzene or substituted benzene in the presence of anhydrous aluminum chloride produces the desired aroyl acid in good yield and purity. More generally, the Friedel and Crafts reaction between an aliphatic dibasic acid anhydride and an aromatic compound results in the formation of an aroyl fatty acid with the aroyl group situated at the last carbon atom of the aliphatic chain.

PREPARATION OF BENZOYLPROPIONIC ACID

In a 2-l, three-necked, round-bottomed flask fitted with a mechanical stirrer and two reflux condensers are placed 68 g. (0.68 mole) of succinic anhydride and 350 g. (4.5 moles) of dry, thiophene-free benzene. The stirrer is started, and 200 g. (1.5 moles) of powdered, anhydrous aluminum chloride is added all at once. Hydrogen chloride is evolved and the mixture becomes hot. It is heated in an oil bath and refluxed, with continued stirring, for half an hour. The flask is then surrounded by cold water, and 300 cc. of water is slowly added from a dropping funnel inserted in the top of one of the condensers.

After the addition of water to the aluminum chloride complex, 100 cc. of concentrated hydrochloric acid (sp. gr. 1.18) is added and the benzene is removed by steam distillation. The hot mixture is transferred to a 2-l beaker, and the 3-benzolypropionic acid separates as a colorless oil which soon solidifies. After cooling to 0° C., it is collected, washed with a cold mixture of 50 cc. of concentrated hydrochloric acid and 150 cc. of water, and then with 200 cc. of cold water. The crude acid is dissolved in a solution of 75 g. of anhydrous sodium carbonate in 500 cc. of water by boiling for fifteen minutes. The solution is filtered with suction and the small amount of aluminum hydroxide washed twice with 50-cc. portions of hot water. Four grams of charcoal is added to the hot filtrate; the solution is stirred for three to four minutes and then filtered with suction. The clear, colorless filtrate is transferred to a 2-l beaker, cooled to 50°–60° C., and carefully acidified with 130 cc. of concentrated hydrochloric acid. After cooling to 0° C. in an ice-salt bath the acid is filtered, washed well with water, dried overnight at room temperature, and finally dried to constant weight at 40°–50° C. The yield is 110–115 g. (92–95 percent of the theoretical amount). It melts at 114°–115° C. and needs no further purification.

Among the more important homologs of 3-benzylpropionic acid which I have prepared are the following acids and (in parenthesis) the hydrocarbons from which they were prepared:

| | |
|---|---|
| 3-(4-methylbenzoyl)propionic acid | (toulene) |
| 3-(4-ethylbenzoyl)propionic acid | (ethylbenzene) |
| 3-(4-propylbenzoyl)propionic acid | (propylbenzene) |
| 3-(4-isopropylbenzoyl)propionic acid | (cumene) |
| 3-(4-butylbenzoyl)propionic acid | (butylbenzene) |
| 3-(4-amylbenzoyl)propionic acid | (amylbenzene) |
| 3-(3,4-dimethylbenzoyl)propionic acid | (o-xylene) |
| 3-(2,4-dimethylbenzoyl)propionic acid | (m-xylene) |
| 3-(2,5-dimethylbenzoyl)propionic acid | (p-xylene) |
| 3-(2,4,6-trimethylbenzoyl)propionic acid | (mesitylene) |

| -continued | |
|---|---|
| 3-(2,3,4,5-tetramethyl-benzoyl)propionic acid | (1,2,3,4, tetra-methylbenzene) |
| 3-(2,3,5,6-tetramethyl-benzoyl)propionic acid | (1,2,4,5 tetra-methylbenzene) |
| 3-(2,3,4,5,6-pentamethyl-benzoyl)propionic acid | (pentamethyl-benzene) |
| 3-(4-phenylbenzoyl)propionic acid | (biphenyl) |
| 3-(4-cyclohexylbenzoyl)propionic acid | (cyclohexyl-benzene) |

Among the substituted benzoylpropionic acids which I have used to prepare various salts are 3-(4-bromobenzoyl) propionic acid, 3-(4-fluorobenzoyl) propionic acid, 3-(4-chlorobenzoyl) propionic acid, and 3-(4-methoxybenzoyl) propionic acid.

It is thought that the alkali metal salts of benzoylpropionic acid form a 7-member ring structure in which the alkali metal cation binds to the keto group. By varying the length of the aliphatic chain from the three carbons of the propionic chain, various size rings are believed to be formed. Various size rings are known to be stressed in varying ways depending on the number, type and position of atoms forming the ring. Usually, the ring with minimal stress is the most stable. In the case of the sensors of present invention, in general the 7-member ring formed by the alkali metal benzoylpropionates is most stable and signals best.

So as to arrive at the most stable and most effective sensors, the salts of acids possessing chains of varying length have been evaluated. Among these acids 4-benzoylbutyric acid, $C_6H_5CO(CH_2)_3CO_2H$, benzoylformic acid, $C_6C_5COCO_2H$, and, of course, 3-benzoylpropionic acid are most useful for preparing humidity-sensing salts for standard applications. Acids having longer chain lengths are suitable for specialized sensor salts.

Introducing other elements in place of carbon in a ring structure is known to also effect the stresses in the ring. Thus, I have investigated the salts of analogs of benzoylpropionic acid in which, for example, nitrogen has replaced carbon. A good example of this is hippuric acid, $C_6H_5CONHCH_2CO_2H$, in which the NH replaces one of the $CH_2$ groups of the propionic acid chain. 4-nitrohippuric acid, $O_2NC_6H_4CONHCH_2CO_2H$ has also been examined. Other compounds of this type but of differing chain lengths, so that rings of varying size are believed to form, include the following:
N-benzoyl-B-alanine, $C_6H_5CONHCH_2CH_2CO_2H$
N-(4-aminobenzoyl)-B-alanine, $H_2NC_6H_4CONHCH_2CH_2CO_2H$
N-(4-nitrobenzoyl)-B-alanine, $O_2NC_6H_5C_6H_4CONHCH_2CH_2CO_2H$
N-(p-nitrobenzoyl)-6-aminocaproic acid, $O_2NC_6H_4CONH(CH_2)_5CO_2H$ Instead of single rings such as are present in benzene or biphenyl, fused rings such as are found in naphthalene can be reacted in form aroyl compounds. Additional compounds whose salts have been evaluated include the following:
gamma-oxo-1-naphthalenebutyric acid, $C_{10}H_7COCH_2CH_2CO_2H$
gamma-oxo-2-naphthalenebutyric acid, $C_{10}H_7COCH_2CH_2CO_2H$
gamma-oxo-1-pyrenebutyric acid, $C_{16}H_9COCH_2CH_2CO_2H$ The study of the physical chemistry of the lattice modifiers which I have discussed before also has added greatly to an understanding of these systems. That is because, as I have already noted, the modifiers closely resemble the side chains attached to the aryl groups of the prime sensing salts. It is believed that the chain of the modifier forms a ring structure in which an alkali metal carbon bonds to an equivalent of the keto group of benzoylpropionic acid. Because of their structural similarity, discoveries in one system assist in the understanding of the other.

Among the acids which have been evaluated as 6-member formers are malonic acid, $HO_2CCH_2CO_2H$, and tartronic acid, $HO_2CCH(OH)CO_2H$. Acids whose salts were investigated and which form 7-member rings include the following:
succinic acid, $HO_2CCH_2CH_2CO_2H$
levulinic acid, $CH_3COCH_2CH_2CO_2H$
ketoglutaric acid, $HO_2CCH_2CH_2COCO_2H$
hydroxybutyric acid, $HOCH_2CH_2CH_2CO_2H$
succinamic acid, $H_2NCOCH_2CH_2CO_2H$
aminobutyric acid, $H_2N(CH_2)_3CO_2H$
Acids whose salts were worked with and which may form 8-member rings are glutaric acid, $HO_2C(CH_2)_3CO_2H$, and its fluorinated derivative, perfluoroglutaric acid, $HO_2C(CH_2)_3CO_2H$. A possible 9-member ring forming salt examined is that of aminocaproic acid, $H_2N(CH_2)_5CO_2H$.

The alkali metal salts of analogs of these same acids, in which a phenyl group replaces a hydrogen of one of the methylene groups, also work well as lattice modifiers. Examples of acids useful for preparing effective lattice modifiers of this type include the following phenylsuccinic acid, phenylmalonic acid, phenylhydroxybutyric acid, and phenylglutaric acid.

From these interrelated studies has been developed a general formula for the acids which form the anions of these humidity sensors:

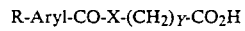

$$R\text{-Aryl-CO-X-}(CH_2)_Y\text{-CO}_2H$$

where R is hydrogen, halogen, alkyl, alkoxy, or a nitro group.
Aryl is phenyl or a connected ring structure such as a biphenyl or a fused ring structure such as naphthalene, acenaphthene, fluorene, anthracene, or pyrene.
X is a nitrogen or a carbon attached to the adjacent methylene with either a single or double bond.
Y is 0 to 7

In a similar way, there has been developed a general formula for the acids whose alkali metal salts comprise the lattice modifiers which allow a smooth and essential reduction of the trigger humidities of the prime sensor salts:

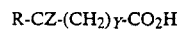

$$R\text{-CZ-}(CH_2)_Y\text{-CO}_2H$$

where R is amino, hydroxyl, carboxyl, or a methyl group.
Z is hydrogen, hydroxyl, or a keto group.
Y is 0 to 4.

I have already given information on the synthesis of the acids which are reacted to form the sensing salts of technology. The preparation of two typical alkali metal salts useful as humidity sensors in the pure state or as componenets of compounded materials follows:

PREPARATION OF CESIUM BENZOYLPROPIONATE 72.0 g. of 99% pure 3-benzoylpropionic acid is slurried in 100 cc. distilled water. 97.3 g. of a 4.11 molar, pure cesium hydroxide solution is added and the temperature raised to 65° C. to obtain complete solution. The solution is filtered through No. 40 filter paper to remove dust, etc. The solution is then evaporated on a hot plate to 200 g., which gives a 2 molar concentration, and it is then bottled.

PREPARATION OF POTASSIUM ETHYLBENZOYLPROPIONATE 83.3 g. of 99% pure 3-(4-ethylbenzolyl) proponic acid is slurred in 100 cc. distilled water. 49.1 g. of 8.144 molar, pure potassium hydroxide solution is added and the temperature is raised to 65° C. to obtain complete solution. The solution is filtered through No. 40 filter paper to remove dust, etc. The solution is then evaporated on a hot plate to 200 g., which gives a 2 molar concentration, and it is then bottled.

The preparation of the salts which I have termed lattice modifiers is equally straightforward.

PREPARATION OF CESIUM LEVULINATE 46.9 gr. of 99% pure levulinic acid is slurried in 100 cc. distilled water. 97.3 g. of a 4.22 molar, pure cesium hydroxide solution is added and the temperature is raised to 65° C. to obtain complete solution. The solution is filtered through No. 40 filter paper to remove dust, etc. The solution is then evaporated on a hot plate to 200 g., which gives a 2 molar concentration, and it is then bottled.

These materials are readily compounded into highly stable solutions which can be readily coated onto a variety of substrates. The preparation of a sensor solution of cesium benzoylpropionate, which triggers optically at 35% RH at 20° C. (when applied as a film, typifies the preparation of sensors usefull for lower RH sensing.

PREPARATION OF A 35% RH SALT SOLUTION

The following materials are weighed together:
120 g. 10% cesium polyacrylate solution
338 g. distilled water
30 g. M/40 zinc acetate solution
12 g. 4% cesium borate
100 g. 2M cesium 3-benzolypropionate
1 g. Monsanto's HB40

Slow speed agitation serves nicely to mix the various major ingredients. However, the HB40 must be dispensed using a high speed mixer.

By dissolving into the compounded sensor salt increasing quantities of a lattice modifier such as cesium levulinate, whose preparation has been described before, the trigger point of the blend can be smoothly and linearly reduced to 15% or less.

The preparation of a sensor solution of potassium 3-(4-ethylbenzoyl) propionate which triggers at 83% RH at 20° C. (when applied as a film) is representative of the preparation of sensors which trigger at higher humidities. The procedure is essentially the same as that described for the 35% RH sensor salt solution.

PREPARATION OF A 83% SENSOR SALT SOLUTION

The following materials are weighed together and processed as before:
120 g. 10% potassium polyacrylate solution
338 g.. distilled water
30 g. M/40 zinc acetate solution
12 g. 4% potassium borate
100 g. 2M potassium 3-(4-ethylbenzoyl) propionate
1 g. Monsanto's HB40

Summarizing, acids can be readily synthesized from which humidity-responsive alkali metal salts can be easily prepared. Solutions of such pure salts can be readily coated onto a variety of substrates to produce primary, non-drifting humidity sensors of great accuracy. The readout can be either in optical or in electrical capacitance changes or in both. The humidity range which such salts can cover is large, and by incorporating readily prepared lattice modifier salts as well, the range is substantially expanded.

Compounding such pure, prime sensing salts and their lattice modifiers with appropriate polymers, heavy metal salts, borates, and lattice stabilizers creates compositions unusually well suited for industrial coating. Such coated substrates can be used in direct readout hygrometers, electronic hygrometric controls, electronic hygrometers, hygrometric limit alarms, and many other devices.

Turning again to the various hygrometric devices which were described earlier in a general way, the simple transmission-type sandwich of FIG. 3 represents an excellent answer to the need for a humidity alarm for the myriad rooms in which are stored goods of value which can be damaged by high relative humidities. The device can be readily hung near a window or a lamp and thus be suitably illuminated. A coating of a sensor composition of 0.01 mm. thickness or less results in a brilliant optical readout.

The reflection-type sandwich of FIG. 4 is a most convenient device to set into the wall of sealed, humidity-sensitive enclosures (such as electrical junctions and switching boxes where condensation of moisture introduces serious electrical and corrosion problems). In such an installation the humidity sensor has free access to the enclosure air, the circular-type polarizer 20 can be readily installed hermetically in a small aperture in the outer wall of the box, and illuminating beam 5 is supplied by room light or by a flashlight.

The graded series of humidity sensors found in the device of FIG. 5 can range from 15% RH or lower to 85% RH or higher. Though the illustration shows 10% RH intervals and a 30% through 90% RH range, compositions having RH intervals of 5%, 2.5%, or any convenient interval can be used. The RH range can also be selected to suit the needs of the particular device. The sensors in the illustration are accompanied by RH legends since the degradation of stored goods is best gauged in terms of the RH to which the goods are exposed. However, the trigger points of the various plaques can be indicated in absolute humidity terms if desired. The sensors of the present invention trigger at aqueous vapor pressures ranging from about 0.1 to 17.5 mm. of mercury at 20° C.

FIG. 6 is a classically simple embodiment of a capacitance-type humidity sensor. As noted before, it offers great accuracy as well as a unique and simple mode of optically checking the electrical integrity of the capacitance-measuring circuitry by noting the capacitance readout at the point of optical phase shift.

Ordinary secondary, capacitance-type, polymeric humidity sensors function by sorbing water vapor. Their capacitance vs. RH curve is substantially non-linear. Thus, complex electrical networks are used in an attempt to correct each hygrometer's readout to a linear one. However, the shape of a polymer's capacitance vs. RH curve changes as the polymer ages. This complex shift cannot be compensated for. Indeed, although so-called "aqueous humidity calibration salts" are furnished with secondary capacitance-type hygrometers in order to aid in field correction for other types of drift, such field compensation is not successful.

In contrast, the primary, humidity-sensing salts of the present invention are highly stable, definite chemical entities. They can be readily used in a pure, uncompounded form in high precision hygrometers of the capacitance-type, of the optical type, or of a combination type.

As an example, pure cesium benzoylpropionate, in the form of a thin film in a sensor 3, such as FIG. 6, generates a strictly linear capacitance vs. RH curve over the RH range of 22% through 72%. An explained before, linear extension of this range is readily accomplished. Further, this simple sensor has the same sensitivity, namely 0.1–0.2 pF/1% RH/sq. mm. of film, as the finest secondary, capacitance-type sensors which have been developed over the years. In short, the new technology offers at low cost a number of unusual features of great importance in the humidity-sensing field.

There are a few important applications for humidity sensors where exceptionally rigorous conditions are encountered during their life cycles. Perhaps the best known example of such unusual circumstances is the 500° C. cycle to which humidity sensor chips are exposed during the hermetic sealing of military-type ceramic "packages" which house integrated circuits. The sensor chips (which have been secondary type sensors until now) are sealed within the package to monitor its interior humidity, the electrical connections being brought out through package pins.

Secondary type capacitive or conductive sensors offer many problems since the sensor within the hermetically sealed package cannot be standardized after firing. Thus, there is a real need for primary type, non-drifting sensors such as those of the present invention. Unfortunately, though the organic type sensors of this invention are exceptionally stable, they cannot withstand 500° C. firing. For such applications I have found inorganic hydrates of great utility. Typical of the chemical compounds which may be used in capacitance-type, humidity-responsive devices which may be cycled to elevated temperatures are these: calcium chloride, barium perchlorate, magnesium perchlorate, calcium sulfate, calcium bromide, and copper sulfate.

Calcium chloride typifies a salt I have found most useful as a capacitance-type sensor since it may be cycled to 500° C. for an extended period and still retain its primary humidity sensing characteristics.

I have found that the finely inorganic compounds which are so useful in compounding the organic sensor salts of the present invention (and which I have discussed before) also are very effective in the compounding of these inorganic salts as to secure high sensitivity and freedom from deliquescence problems. It is theorized that the sensor coatings of these very high surface area materials are only a few molecules thick and so are very responsive. As an example, a 0.25 molar solution of chemically pure calcium chloride, thickened with from about 0.5 to 4.0 percent by weight of a pyrogenic silica (200 sq. meters surface area/g.) forms a most effective coating suspension. The curve of capacitance vs. RH of such a sensing film gradually slopes upward from about 5% RH to 15% RH at which point there is a large and almost vertical rise before resuming a linear slope. It is an excellent curve with which to track the critical 8 to 20% RH range within the "sealed" package so as to easily detect micro leaks.

I have found that calcuim bromide generates a capacitance vs. RH curve which is of the same characteristic shape as that of calcium chloride, FIG. 8c, when compounded with the same silica. However, the large and almost vertical rise occurs at about 5% RH at 20° C. instead of the 15% RH characteristic of calcium chloride. Further, I have found that calcium chloride and bromide may be blended so as to secure capacitance vs. RH curves in which the large rise occurs at intermediate humidities.

In summary, and as has been previously discussed, to create a graded series of humidity sensors where optical trigger points vary from 15% RH to 85%, I typically select a sensor salt from the potassium and/or cesium alkali metal salts of benzoylpropionic acid and/or ethylbenzoylpropionic acid, stabilize it with an alkali metal perfluoralkyl acid phosphate, complex it with the alkali metal salt of a polymer with repetitive carboxyl groups whose acidic hydrogens have been replaced by the alkali metal cations (and which has been complexed with a selected polyvalent cation of a water soluble salt such as copper acetate along with an alkali metal borate), and, if desired, reduce its trigger humidity by adding a crystal modifier such as cesium hydroxybutyrate.

I claim:

1. A combination optical and capacitance humidity-responsive device for selectively and directly monitoring optical and electrical changes in a chemical composition comprising (1) a source of illumination providing a light beam, (2) a chemical composition comprising a lyotropic liquid crystal salt having an organic ring portion that is hydrophobic and a polar head that is hydrophilic and which of itself reversibly senses changes in humidity, the combination being triggered optically at a particular water vapor pressure/temperature from an anisotropic and translucent liquid crystal state characteristic of a first water vapor pressure/temperature condition immediately contiguous to said particular water vapor pressure/temperature to an isotropic and transparent liquid state characteristic of the particular water vapor pressure/temperature, while its dielectric constant is changing substantially and reproducibly as the water vapor pressure/temperature changes, (3) light detecting means for detecting observable changes in the brightness and intensity of the light coming from the composition when the light beam contacts the composition, the light from the composition at the first water vapor pressure/temperature being of sufficient brightness and intensity to provide a visual signal at the first water vapor pressure/temperature but not at the particular water vapor pressure/temperature, (4) electrode means insulated from the composition and capacitively associated therewith and means for impressing a voltage across said electrode means and (5) electrical capacitance measuring means connected to said electrode means for measuring changes in the dielectric constant of the composition in response to changes in the water vapor pressure/temperature of said composition.

2. A device as defined in claim 1 in which the composition is birefringent at the immediately contiguous water vapor pressure/temperature when in a liquid crystal state and non-birefringent at the particular water vapor pressure/temperature when liquid.

3. A device as defined in claim 1 in which the means for detecting observable changes includes means for illuminating the composition which when translucent at the immediately contiguous water vapor pressure/temperature provides light of sufficient intensity and brightness to provide a visual signal.

4. A device as defined in claim 1 in which the light detecting means includes electrical means responsive to the visual signal at the immediately contiguous water vapor pressure/temperature and non-responsive to the signal at the particular water vapor pressure/temperature.

5. A device as defined in claim 1 in which the electrical capacitance measuring means is calibrated in percent relative humidity.

6. A device as defined in claim 1 and wherein the electrical capacitance measuring means includes an LED activated by the light detecting means to visually indicate that said particular water vapor pressure/temperature has been reached to thereby confirm the operation of the electronic circuitry in its measurement of both optical and electrical parameters.

7. A device as defined in claim 1 in which the chemical composition is a mixture of an alkali metal salt of 3-benzoylpropionic acid and a lattice modifier which is an alkali metal salt of hydroxybutyric acid.

8. A device as defined in claim 1 in which the chemical composition is a mixture of an alkali metal salt of 3-benzoylpropionic acid and a lattice modifier which is an alkali metal salt of one or more carboxylic acids selected from the group consisting of malonic, tartronic, succinic, levulinic, ketoglutaric, hydroxybutyric, succinamic, and aminobutyric acids.

9. A device as defined in claim 1 in which the chemical composition comprises a mixture of an alkali metal salt of 3-benzoylpropionic acid and 3-(4-ethylbenzoyl) propionic acid.

10. A device as defined in claim 1 in which the saturated aqueous solution of the composition has a vapor pressure in the range of about 0.1 to 17.5 mm. of mercury of 20° C.

11. A device as defined in claim 1 in which the composition is a coating of approximately 0.01 mm. thickness on a translucent or transparent, isotropic substrate.

12. A device as defined in claim 1 in which the chemical composition is a mixture of the alkali metal salts of 3-benzoylpropionic acid, of a lattice modifier which is an alkali metal salt of hydroxybutyric acid, of a lattice stabilizer comprising an alkali metal salt of a perfluoroalkyl acid phosphate at a concentration of 0.1 to 0.3% by weight, on the basis of solids, and of a complex comprising (a) a water-soluble salt of $Cu^{++}$ at a concentration of 0.4 to 5.0 mol percent of the metals present in the chemical composition, (b) an alkali metal salt of polyacrylic acid in a concentration of from 2.0 to 8.0% by weight for each 8% of the alkali metal salt of the 3-benzoylpropionic acid, and (c) an alkali metal borate in concentration of from 0.25 to 10.0 mol percent of the metals present in the chemical composition.

13. A device as defined in claim 1 in which the composition is the potassium salt of 3-benzoyl propionic acid.

14. A device as defined in claim 13 in which the composition is translucent at the immediately contiguous water vapor pressure/temperature when less hydrated transparent at the particular water vapor pressure/temperature when hydrated.

15. A device as defined in claim 13 in which the composition is translucent at the immediately contiguous water vapor pressure/temperature when crystalline and transparent at the particular water vapor pressure/temperature when liquid.

16. A device as defined in claim 1 in which the capacitance measuring means includes adjustable electrical means responsive to the capacitance signal at the immediately contiguous water vapor pressure/temperature but non-responsive to the capacitance signal at the particular water vapor pressure/temperature.

17. A device as defined in claim 16 in which the electrical means includes control means that is responsive to the capacitance signal for controlling electrical power to activate an electrical circuit.

18. A capacitance, humidity-responsive device comprising means for providing observable changes in humidity comprising (1) a chemical composition comprising a lyotropic liquid crystal salt having an organic ring portion that is hydrophobic and a polar head that is hydrophilic and which of itself reversibly senses changes in humidity, the composition being triggered optically at a particular water vapor pressure/temperature from an anisotropic and translucent liquid crystal state characteristic of a first water vapor pressure/temperature condition immediately contiguous to said particular water vapor pressure/temperature to an isotropic and transparent liquid state characteristic of the particular water vapor pressure/temperature, while its dielectric constant is changing substantially and reproducibly as the water vapor pressure/temperature changes, (2) electrode means insulated from the composition and capactively associated with said composition, and electrical means for impressing a voltage across said electrode means, and (3) electrical capacitance measuring means connected to said electrode means for measuring changes in the dielectric constant of the composition in response to changes in the water vapor pressure/temperature of said composition.

19. A device as defined in claim 18 in which all elements of the device have been miniaturized, and the electrical capacitance measuring means for measuring changes in the dielectric constant of the composition is an intergrated circuit.

20. A humidity-responsive device as defined in claims 1 or 18 and wherein the chemical composition comprises one or more alkali metal salts of an acid of the general formula R-Aryl-CO-X-$(CH_2)_Y$-$CO_2H$, where R is hydrogen, halogen, alkyl, alkoxy, or nitro, where Aryl is phenyl or a connected ring structure or a fused ring structure, where X is a nitrogen or a carbon attached to the adjacent methylene with either a single or double bond, and where Y is 0 to 7.

21. A device as defined in claims 1 or 18 in which at least two discrete adjacent areas capacitively associated with the electrode means are occupied with compositions comprising a series of compounds or mixtures of compounds which trigger at different water vapor pressures at 20° C.

22. A device as defined in claims 1 or 18 in which the chemical composition contains before coating from 10–50% by weight of sensor solids compounded with from 0.5 to 4.0% by weight of inorganic compounds of high surface area.

23. An optical humidity-responsive device comprising (1) a source of illumination providing a light beam, (2) means for providing observable changes in humidity comprising a chemical composition which comprises one or more alkali metal salts of an acid of the general formula R-Aryl-CO-X-$(CH_2)_Y$-$CO_2H$, where R is hydrogen, halogen, alkyl, alkoxy, or nitro, where Aryl is phenyl or a connected ring structure or a fused ring structure, where X is a nitrogen or a carbon attached to the adjacent methylene with either a single or a double bond, and where Y is 0 to 7 and which composition of itself reversibly senses changes in humidity, said composition being triggered optically at a particular water vapor pressure/temperature from an anisotropic and translucent phase characteristic of a first water vapor pressure/temperature condition immediately contiguous to said particular water vapor pressure/temperature to an isotropic and transparent phase characteristic of the particular water vapor pressure/temperature, and (3) light detecting means for detecting observable changes in the brightness and intensity of the light coming from the composition when the light beam contacts the composition, the light from the composition at the first water vapor pressure/temperature being of sufficient brightness and intensity to provide a visual signal at the first water vapor pressure/temperature but not at the particular water vapor pressure/temperature.

24. An optical humidity-responsive device as defined in claim 23 and wherein the connected ring structure is biphenyl.

25. An optical humidity-responsive device as defined in claim 23 and wherein the fused ring structure is of the group consisting of naphthalene, acenaphthene, fluorene, anthracene and pyrene.

26. A device as defined in claim 23 and comprising a rectangularly shaped solid, isotropic material having a cross-section which causes internal reflection of light when such light is directed to its front, at least 25% of the device's back side being coated with the composition having a thickness of approximately 0.01 mm.

27. A device as defined in claim 26 in which the cross-section of the isotropic material is one of the group consisting of semi-circular, semi-annular or trapezoidal.

28. A device as defined in claim 26 and wherein the selected cross-section is trapezoidal and the angles of the trapezoid being selected so as to secure total internal reflection of light within the material.

29. A device as defined in claim 20 or 23 in which the trigger point of the chemical composition is reduced to a lower water vapor pressure/temperature through the inclusion of a lattice modifier which comprises one or more of the alkali metal salts of an acid of the general formula $R\text{-}CZ\text{-}(CH_2)_Y\text{-}CO_2H$, where R is amino, hydroxyl, carboxyl, or methyl, where Z is hydrogen, hydroxyl, or a keto, and where Y is 0 to 4.

30. A device as defined in claims 23 or 20 in which the composition is optically stabilized through the inclusion of from 1.0 to 3.0% by weight, on the basis of solids of a lattice stabilizer which comprises a low vapor pressure aryl hydrocarbon from the group consisting of: hydrogenated terphenyl, terphenyl, 1,1-di(orho-xylyl) ethane, 1,2,3,4 tetramethyl benzene, 1,2,4,5 tetramethylbenzene, 1,2,3,5 tetramethyl benzene, 1,2,3,4,5 pentamethylbenzene, and cyclohexylbenzene.

31. A device as defined in claims 23 or 20 in which the composition is optically stabilized through the inclusion of from 0.1 to 0.3% by weight, on the basis of solids, of a lattice stabilizer from the group consisting of alkali metal perfluoralkyl sulfonates, carboxylates, and acid phosphates, whose fluorocarbon chains contain 3 to 5 carbons.

32. A device as defined in claims 23 or 20 in which the chemical composition is complexed with from 0.4 to 5.0 mol percent of the metals present of a water-soluble salt of a polyvalent cation selected from the group consisting of $Cu^{++}$, $Ni^{++}$, $Co^{++}$, $Mn^{++}$, $Al^{+++}$, $Zn^{++}$, and $Cr^{+++}$, and in which each 8% of alkali metal sensor salt is complexed with from 2.0 to 8.0% by weight of a polymer which has repetitive carboxyl groups whose acidic hydrogens have been replaced by alkali metal cations, and in which the chemical composition is complexed with an alkali metal borate in an amount from 0.25 to 10.0 mol percent of the metals present.

33. A device as defined in claims 23 or 20 in which the composition comprises an alkali metal salt of 3-benzoylpropionic acid.

34. A device as defined in claims 23 or 20 in which the composition comprises mixtures of the alkali metal salts of 3-benzoylpropionic acid.

35. A device as defined in claims 23 or 20 in which the composition comprises an alkali metal salt of 3-(4-ethylbenzoyl) propionic acid.

36. A device as defined in claims 23 or 20 in which the composition comprises mixtures of the alkali metal salts of 3-(4-ethylbenzoyl) propionic acid.

37. An optical humidity-responsive device comprising (1) a source of illumination providing a light beam, (2) means for providing observable changes in humidity comprising a chemical composition which comprises one or more alkali metal salts of an acid of the general formula $R\text{-}Aryl\text{-}CO\text{-}X\text{-}(CH_2)_Y\text{-}CO_2H$, where R is one of the group consisting of hydrogen, halogen, alkyl, alkoxy, or nitro, where Aryl is phenyl or a connected ring structure or a fused ring structure, where X is a nitrogen or a carbon attached to the adjacent methylene with either a single or a double bond, and where Y is 0 to 7 and which composition of itself reversibly senses changes in humidity, said composition being triggered optically at a particular water vapor pressure/temperature from an anisotropic and translucent phase characteristic of a first water vapor pressure/temperature condition immediately contiguous to said particular water vapor pressure/temperature to an isotropic and transparent phase characteristic of the particular water vapor pressure/temperature, (3) means to amplify observable changes in the composition due to changes in the humidity including a polarizer for the light beam and an analyzer for the polarized beam that is passed through the composition, and (4) light detecting means for detecting observable changes in the brightness and intensity of the light coming from the composition when the light beam contacts the composition, the light from the composition at the first water vapor pressure/temperature being of sufficient brightness and intensity to provide a visual signal at the first water vapor pressure/temperature but not at the particular water vapor pressure/temperature.

38. A device as defined in claim 37 in which the device is a transmission type in which the light beam passes through the polarizer and the polarized light beam passes through the composition, where it is doubly refracted at the first water vapor pressure/temperature, and the emerging refracted beam passes through the analyzer.

39. A device as defined in claim 37 in which the device is a reflective type, the light beam passes through a circular polarizer and the composition to a mirror and then being reflected back through the composition and the analyzer.

40. A device as defined in claim 37 and wherein the connected ring structure is biphenyl.

41. A device as defined in claim 37 and wherein the fused ring structure is of the group consisting of naphthalene, acenaphthene, fluorene, anthracene and pyrene.

* * * * *